US012649040B2

(12) United States Patent
Haibach et al.

(10) Patent No.: US 12,649,040 B2
(45) Date of Patent: Jun. 9, 2026

(54) MAGNETIC FASTENING ARRANGEMENTS FOR SECURING PATIENT INTERFACE DEVICES

(71) Applicant: KONINKLIJKE PHILIPS N.V., Eindhoven (NL)

(72) Inventors: Richard Thomas Haibach, Verona, PA (US); Joyce Van Zanten, Waalre (NL); Nicolaas Petrus Willard, Valkenswaard (NL); Marco Baragona, Delft (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 744 days.

(21) Appl. No.: 18/071,731

(22) Filed: Nov. 30, 2022

(65) Prior Publication Data

US 2023/0201509 A1     Jun. 29, 2023

Related U.S. Application Data

(60) Provisional application No. 63/294,587, filed on Dec. 29, 2021.

(51) Int. Cl.
A61M 16/06          (2006.01)
(52) U.S. Cl.
CPC . A61M 16/0683 (2013.01); *A61M 2205/0272* (2013.01)
(58) Field of Classification Search
CPC ........... A61B 5/0205; A61M 16/0051; A61M 16/0057; A61M 16/0069; A61M 16/024; A61M 16/06; A61M 16/0605; A61M 16/0622; A61M 16/0633; A61M 16/0666;
A61M 16/0683; A61M 16/0688; A61M 16/08; A61M 16/0816; A61M 16/0875; A61M 16/10; A61M 16/1005; A61M 16/1045; A61M 16/1055; A61M 16/107; A61M 16/109; A61M 16/1095; A61M 16/16; A61M 16/208; A61M 2016/0027; A61M 2016/0033; A61M 2205/0216; A61M 2205/0272; A61M 2205/15;
(Continued)

(56) References Cited

U.S. PATENT DOCUMENTS

| | | | | |
|---|---|---|---|---|
| 10,232,137 B2 * | 3/2019 | Romagnoli | ....... | A61M 16/0633 |
| 10,953,180 B2 * | 3/2021 | Foong | ............... | A61M 16/0666 |

(Continued)

FOREIGN PATENT DOCUMENTS

| | | | | |
|---|---|---|---|---|
| WO | WO-2018072205 A1 * | 4/2018 | ........... | A61B 5/0205 |

*Primary Examiner* — Annette Dixon
(74) *Attorney, Agent, or Firm* — Michael W. Haas

(57) ABSTRACT

A coupling arrangement for use in securing a patient interface to the head of a patient. The fastening arrangement includes a first component having a source of a magnetic field and a second component having a mating component attracted to the source by the magnetic field. One or both of the source and/or a portion of the first component is moveable among: a shielded positioning wherein the source is shielded such that the maximum strength of the magnetic field outside of the first component is less than a predetermined value, and an unshielded positioning wherein the source is unshielded such that the maximum strength of the magnetic field outside of the first component is greater than or equal to the predetermined value.

14 Claims, 5 Drawing Sheets

(58) Field of Classification Search
CPC .......... A61M 2205/18; A61M 2205/21; A61M
2205/3368; A61M 2205/3379; A61M
2205/3553; A61M 2205/502; A61M
2205/586; A61M 2205/6063; A61M
2205/7545; A62B 18/084; G06F 1/16
See application file for complete search history.

(56) References Cited

U.S. PATENT DOCUMENTS

| | | | |
|---|---|---|---|
| 2006/0174892 A1 * | 8/2006 | Leksutin .............. | A62B 18/084 |
| | | | 128/207.18 |
| 2014/0283826 A1 * | 9/2014 | Murray ............. | A61M 16/0683 |
| | | | 128/202.27 |
| 2015/0250972 A1 * | 9/2015 | Haibach ............ | A61M 16/0622 |
| | | | 128/202.27 |

* cited by examiner

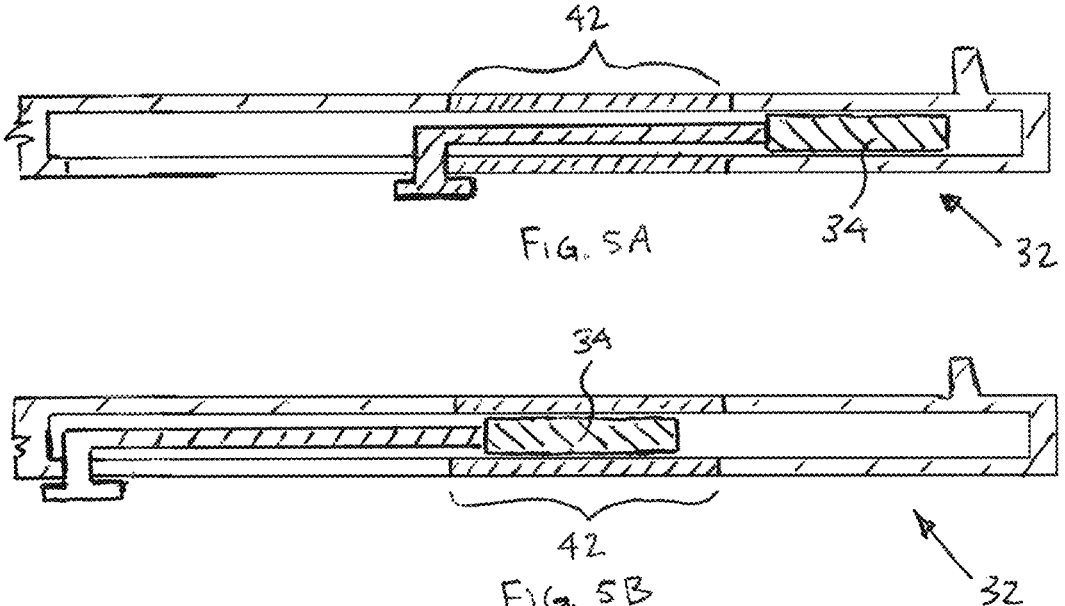
FIG. 5A
FIG. 5B
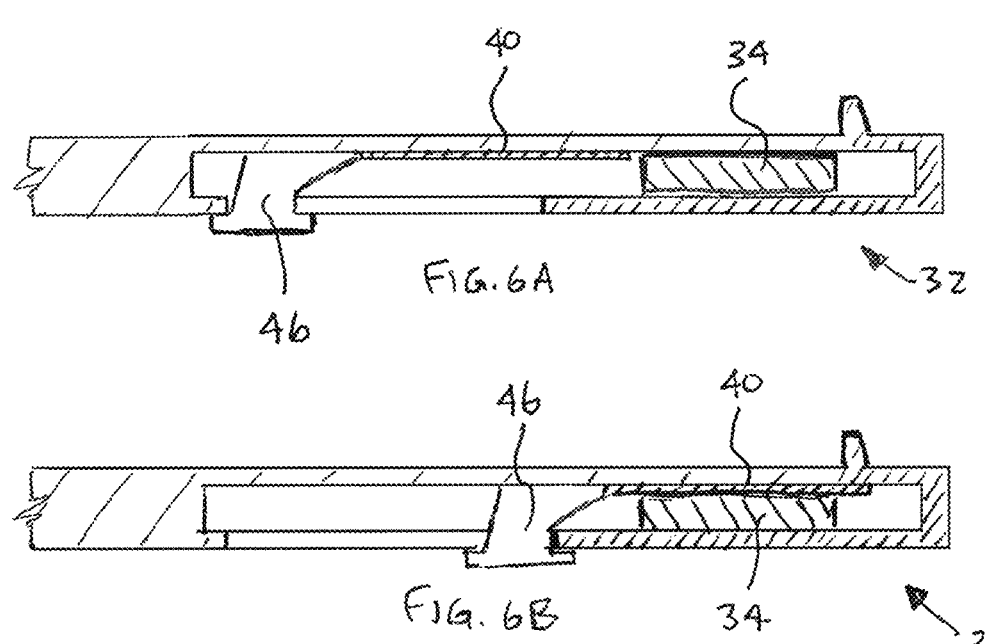
FIG. 6A
FIG. 6B

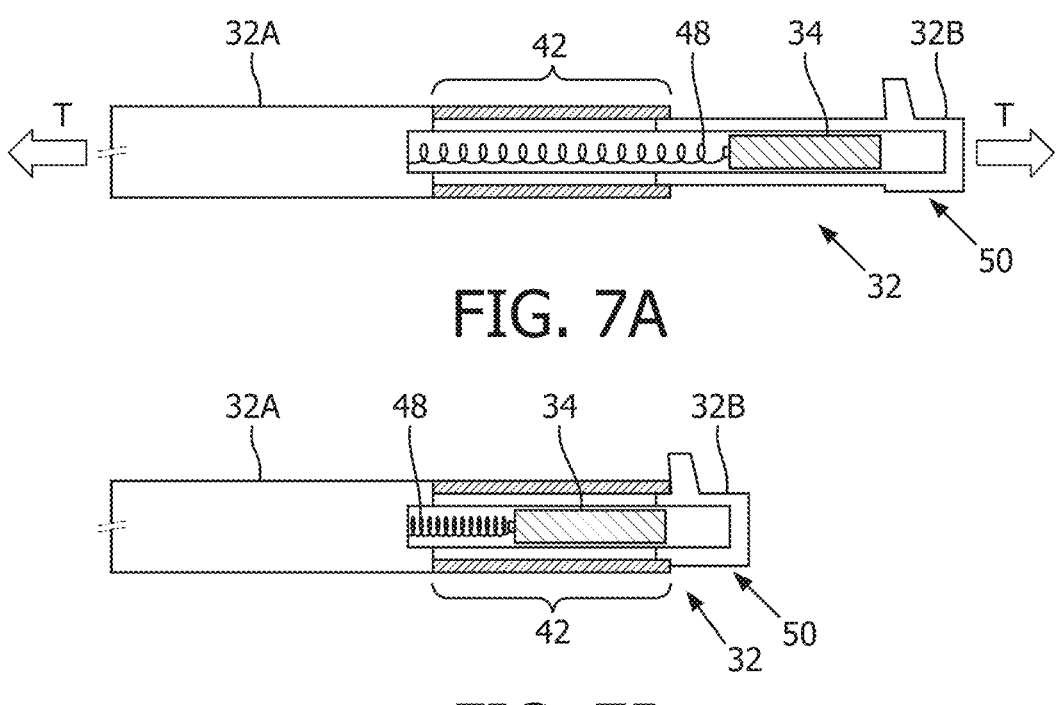
FIG. 7A
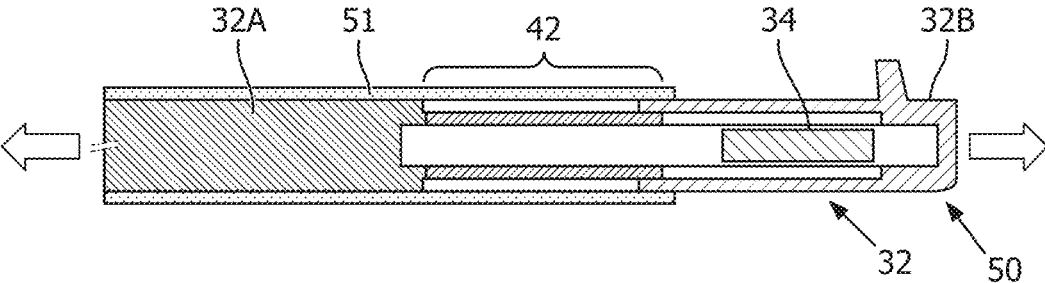
FIG. 7B
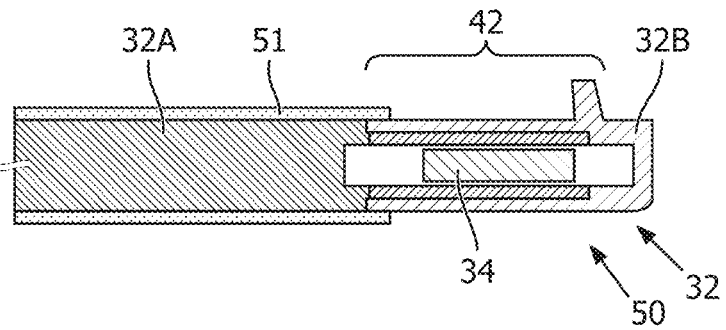
FIG. 8A
FIG. 8B

MAGNETIC FASTENING ARRANGEMENTS FOR SECURING PATIENT INTERFACE DEVICES

CROSS-REFERENCE TO RELATED APPLICATIONS

This patent application claims the priority benefit under 35 U.S.C. § 119(e) of U.S. Provisional Application No. 62/294,587, filed on Dec. 29, 2021, the contents of which are herein incorporated by reference.

BACKGROUND OF THE INVENTION

1. Field of the Invention

The present invention pertains to masks for use in delivering a flow of a breathing gas to an airway of a patient, and, more particularly, to the headgear of such masks that are used to secure the patient interfaces, also of such masks, to the head of a patient. Even more particularly, the present invention pertains to fastening arrangements for use in such headgear that selectively shields sources of magnetic fields utilized therein.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur when there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface including a mask component having a soft, flexible sealing cushion on the face of the patient. The mask component may be, without limitation, a nasal pillow mask, a nasal mask that covers the patient's nose, a nasal/oral mask that covers the patient's nose and mouth, or a full face mask that covers the patient's face. The patient interface is connected to a gas delivery tube or conduit and interfaces the pressure support device with the airway of the patient, so that a flow of breathing gas can be delivered from the pressure/flow generating device to the airway of the patient via the patient interface. Such patient interfaces may also employ other patient contacting components, such as forehead supports, cheek pads and chin pads.

The patient interface is typically secured to the patient's head by a headgear component, typically referred to simply as headgear. The headgear serves not only to secure the patient interface to the patient's head but also serves to provide stability to the patient interface, as instability of the patient interface can result in leaks and discomfort to the patient. A key factor in providing any pressure support therapy is to maintain good mask comfort, seal and stability such that the patient is not disturbed in his or her sleep and the device functions properly. Various fastening arrangements are commonly utilized in headgear, both for connecting components of the headgear to each other, as well as in connecting the headgear to the patient interface, depending on the particular application. To enhance patient experience when putting a mask on and off, magnets have been introduced in such fastening arrangements. This helps in keeping the mask straps on the same force/distance (without having to readjust each time the mask is taken off and put on again).

For some patients however, the use of magnets can lead to unwanted side effects. Some examples of patients that could be negatively affected by the use of magnets are patients with pacemakers, defibrillators, cerebrospinal fluid shunts, cochlear implants, and/or other electronic devices. There are indications that some patients have experienced changes to the pacemaker during the night when wearing a CPAP mask with magnets—the precise issue is that pacemakers have been experiencing activation of their magnet response mode. One potential cause could be that the magnets that are located at the end of the headgear straps when not connected to the patient interface device come very close to the pacemaker device. Therefore a solution that would prevent the magnets of the headgear or mask to become too close to any medical device or a solution that would reduce the magnetic strength of the magnets in patient interfaces to below harmful magnitudes would benefit patients with such medical devices.

SUMMARY OF THE INVENTION

Embodiments of the present invention improve upon known arrangements and address shortcomings such as previously described by shielding magnetic materials used in fastening arrangements when such arrangements are unfastened and thus potentially free to interfere with magnetically sensitive devices.

As one aspect of the present invention, a coupling arrangement for use in securing a patient interface to the head of a patient is provided. The coupling arrangement comprises: a first component comprising a source of a magnetic field; and a second component comprising a mating component attracted to the source by the magnetic field, wherein one or both of the source and/or a portion of the first component is moveable among: a shielded positioning wherein the source is shielded such that the maximum strength of the magnetic field outside of the first component is less than a predetermined value, and an unshielded positioning wherein the source is unshielded such that the maximum strength of the magnetic field outside of the first component is greater than or equal to the predetermined value.

The source may be moveable among the shielded positioning and the unshielded positioning.

The source may comprise a permanent magnet.

The portion of the first component may be moveable among the shielded positioning and the unshielded positioning.

The portion may be a shield member.

The second portion may comprise a patient interface.

The first portion may comprise a frame member of a headgear arrangement.

One or both of the source and/or the portion of the first component may be moveable in a sliding motion among the shielded and unshielded positionings.

The first component may comprise: a main body portion having a shielded region defined therein, and an end portion slidably coupled to the main body portion, the end portion having the source coupled therein; and the end portion and the source may be moveable among the shielded positioning and the unshielded positioning. The first component may further comprise a biasing element biasing the end portion and the source in the shielded positioning. The biasing element may be provided as an internal element of the first component. The biasing element may be provided as an external element of the first component.

The first component may comprise a hinge portion structured to provide for the portion of the first component and the source to move among the shielded and unshielded positionings. The hinge portion may be structured to bias the portion of the first component and the source in the shielded positioning.

As another aspect of the present invention, a mask for communicating a flow of breathing gas to an airway of a patient is provided. The mask having a coupling arrangement as previously described.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 5A is a sectional view of a first component of a coupling arrangement in accordance with one example embodiment of the present invention shown with a source of a magnetic field in an unshielded positioning;

FIG. 5B is a sectional view of the first component of FIG. 5A shown with the source of the magnetic field positioned in a shielded positioning;

FIG. 6A is a sectional view of a first component of a coupling arrangement in accordance with one example embodiment of the present invention shown with a source of a magnetic field in an unshielded positioning;

FIG. 6B is a sectional view of the first component of FIG. 6A shown with the source of the magnetic field positioned in a shielded positioning;

FIG. 7A is a schematic sectional view of a first component of a coupling arrangement in accordance with one example embodiment of the present invention shown with a source of a magnetic field in an unshielded positioning;

FIG. 7B is a schematic sectional view of the first component of FIG. 7A shown with the source of the magnetic field positioned in a shielded positioning;

FIG. 8A is a schematic sectional view of a first component of a coupling arrangement in accordance with one example embodiment of the present invention shown with a source of a magnetic field in an unshielded positioning;

FIG. 8B is a schematic sectional view of the first component of FIG. 8A shown with the source of the magnetic field positioned in a shielded positioning;

DETAILED DESCRIPTION OF EXEMPLARY EMBODIMENTS

Figure 1:
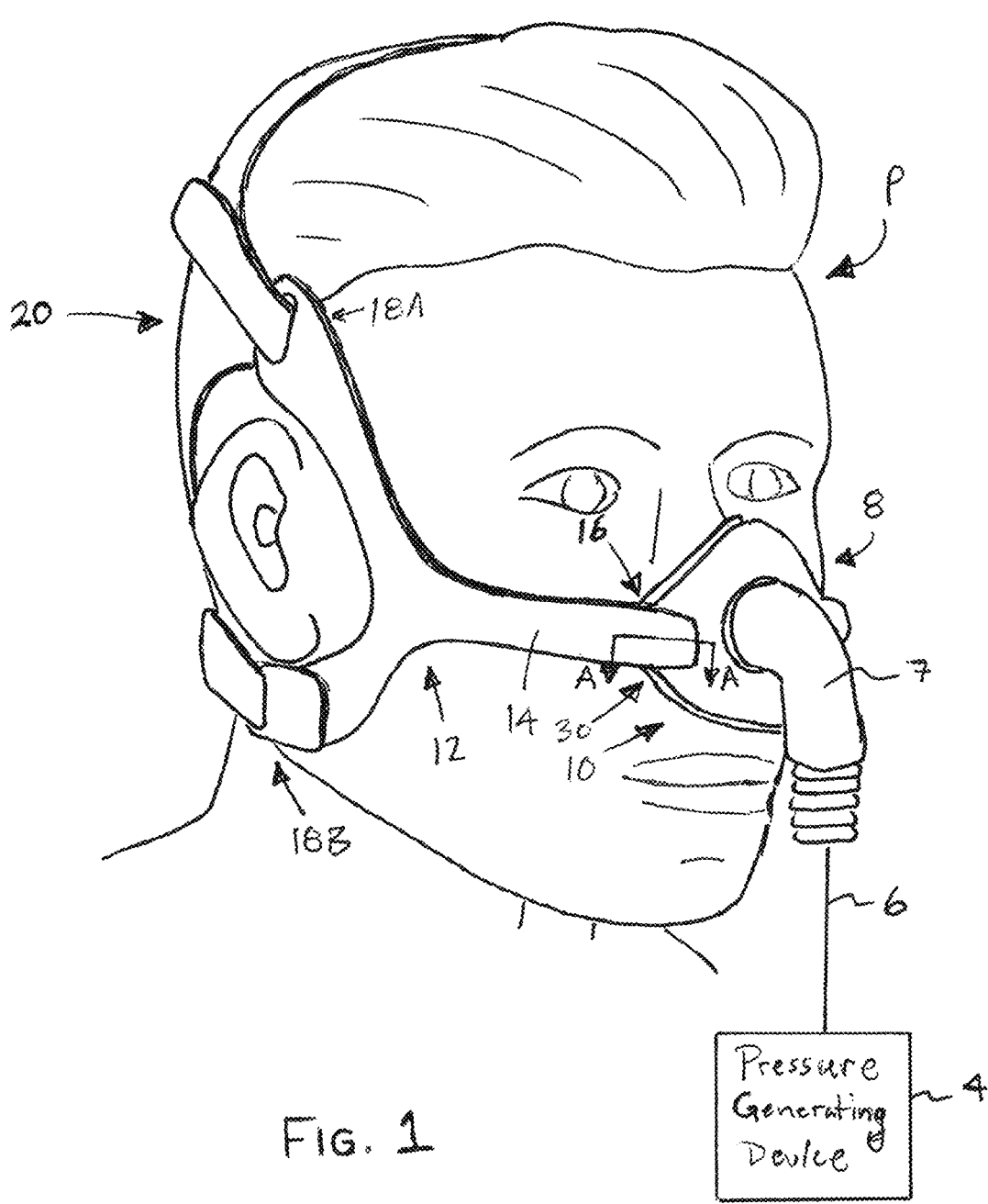
FIG. 1 is a partially schematic depiction of a respiratory interface system adapted to provide a regimen of respiratory therapy to a user/patient shown with a mask thereof positioned on the head of a patient.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, the statement that two or more parts or components "engage" one another shall means that the parts exert a force against one another either directly or through one or more intermediate parts or components.

As used herein, the word "unitary" means a component is created as a single piece or unit. That is, a component that includes pieces that are created separately and then coupled together as a unit is not a "unitary" component or body.

As used herein, the term "number" shall mean one or an integer greater than one (i.e., a plurality).

As used herein, a "coupling assembly" includes two or more couplings or coupling components. The components of a coupling or coupling assembly are generally not part of the same element or other component. As such the components of a "coupling assembly" may not be described at the same time in the following description.

As used herein, a "coupling" is one element of a coupling assembly. That is, a coupling assembly includes at least two components, or coupling components, that are structured to be coupled together. It is understood that the elements of a coupling assembly are compatible with each other. For example, in a coupling assembly, if one coupling element is a snap socket, the other coupling element is a snap plug.

As used herein, "correspond" indicates that two structural components are sized and shaped to be similar to each other and may be coupled with a minimum amount of friction. Thus, an opening which "corresponds" to a member is sized slightly larger than the member so that the member may pass through the opening with a minimum amount of friction. This definition is modified if the two components are said to fit "snugly" together or "snuggly correspond." In that situation, the difference between the size of the components is even smaller whereby the amount of friction increases. If the element defining the opening and/or the component inserted into the opening is/are made from a deformable or compressible material, the opening may even be slightly smaller than the component being inserted into the opening. This definition is further modified if the two components are said to "substantially correspond." "Substantially correspond" means that the size of the opening is very close to the size of the element inserted therein. That is, not so close as to cause substantial friction, as with a snug fit, but with more contact and friction than a "corresponding fit," i.e. a "slightly larger" fit.

A respiratory interface system 2 adapted to provide a regimen of respiratory therapy to a user/patient P in accordance with one example embodiment of the present invention is shown in FIG. 1. Respiratory interface system 2 includes a pressure generating device 4 (shown schematically) and a delivery conduit 6 (shown partially schematically) having a first end (not numbered) coupled to pressure generating device 4 and an opposite second end (not numbered) coupled to a mask 8. Pressure generating device 4 is structured to generate a flow of positive pressure breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, PA), and auto-titration pressure support devices. Delivery conduit 6 is structured to communicate the flow of breathing gas from pressure generating device 4 to mask 8 (e.g., via an elbow 7 or other suitable connector), and mask 8 is structured to further communicate the flow of breathing gas received from delivery conduit 6 to an airway of patient P. Delivery conduit 6 and mask 8 are often collectively referred to as a patient circuit.

Mask 8 is generally of a conventional design aside from portions noted below and includes a patient interface 10 and a headgear arrangement 12 for securing patient interface 10 to the head of patient P. Patient interface 10 is structured to engage about the nose and/or mouth of patient P and is coupled to delivery conduit 6 (e.g., via elbow 7) so as to receive the flow of positive pressure breathing gas produced by pressure generating device 4 via delivery conduit 6 and communicate such flow to the airway of patient P. In the example shown in FIG. 1, patient interface 10 is shown as engaging about only the nose of patient P, however, it is to be appreciated that patient interface 10 may be of any suitable arrangement for providing the flow of positive pressure breathing gas to the nose and/or mouth of patient P without varying from the scope of the present invention. The example headgear arrangement 12 includes a pair of flexible frame members 14 (only the one positioned on the right side of the head of patent P is fully shown FIG. 1).

Each frame member 14 is positioned on a respective side of the head of patient P and extends rearward from patient interface 10 to about a respective ear of patient P. A forward portion 16 of each frame member 14 is selectively coupled to patient interface 10 via a coupling arrangement 30 in accordance with an example embodiment of the present invention as discussed in detail below. Rearward portions 18A and 18B of each frame member 14 is adjustably coupled to a rear headgear portion 20 that extends around the back the head of patient P generally from one ear to the other ear. Although a particular headgear arrangement 12 is illustrated herein, it is to be appreciated that the novel aspects of coupling arrangement 30 discussed below may be incorporated into other headgear arrangements without varying from the scope of the present invention.

It is also to be appreciated that the novel aspects of coupling arrangement 30 may be readily incorporated into generally any coupling point within a headgear arrangement between any components thereof (e.g., frame members, strap members, etc.) and/or between any components thereof and an associated patient interface without varying from the scope of the present invention.

Figure 2:
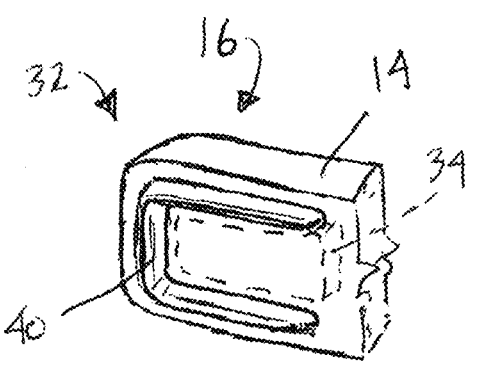
FIG. 2 is a partially schematic perspective view of a first component of a coupling arrangement in accordance with one example embodiment of the present invention.
Figure 3:
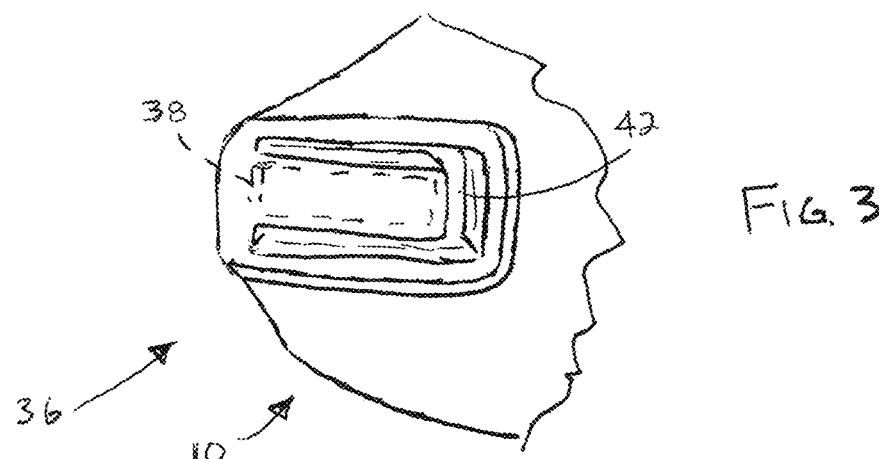
FIG. 3 is a partially schematic perspective view of a second component of a coupling arrangement in accordance with one example embodiment of the present invention.
Figure 4:
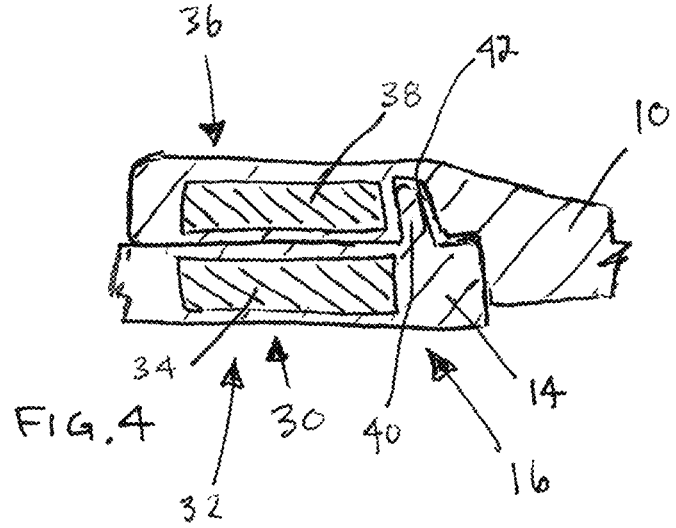
FIG. 4 is a partially sectional view of a coupling arrangement in accordance with one example embodiment of the present invention taken along line A-A of FIG. 1 shown with a source of a magnetic field in a non-shielded position.

Referring now to FIGS. 2-4, similar to conventional arrangements, coupling arrangement 30 includes a first component 32, which in the example embodiment of FIGS. 1-4 is the forward portion 16 of frame member 14, having a source 34 (shown schematically) of a magnetic field (not labeled). In example embodiments, first component 32 is formed primarily from plastic, silicone, or other suitable materials and source 34 is a permanent magnet (or other suitable arrangement for producing a magnetic field). Coupling arrangement 30 further includes a second component 36, which in the example embodiment of FIGS. 1-4 is patient interface 10, having a mating component 38 (shown schematically) which interacts with the magnetic field produced by source 34 such that source 34 and mating component 38 are magnetically attracted toward each other, thus coupling first and second components 32 and 36 together as shown in FIGS. 1 and 4. First and second components may further include cooperating ridge and groove components 40 and 42 or other suitable arrangement(s) that interact to provide for a force to be transferred generally across coupling arrangement 30. As such additional structures are generally not the focus of the present invention they will not be discussed in further detail herein.

Unlike conventional arrangements, first component 32 of coupling arrangement 30 is arranged such that source 34 can be selectively shielded in a manner such that the magnetic field produced by source 34 is contained (to at least a predetermined safe extent) within the first component 32, thus reducing the magnetic strength of source 34 to below a potentially harmful magnitude when not engaged with second component 36. As will be appreciated from the following examples showing various embodiments of first component 32 that may be employed in coupling arrangement 30, such selective shielding of source 34 is generally accomplished by moving one or both of: source 34 relative to a shield member 40 and/or a shielded region 42 (e.g., formed from a mu-metal or other suitable material or materials) between a shielded and unshielded position (relative to the environment adjacent first component 32), and/or moving shield member 40 between a shielding and non-shielding position relative to source 34. As used herein, a "shielded" position is one in which the strength, outside of the shielding, of magnetic fields from a source is less than the strength of such magnetic fields would be if the shielding were not present, i.e., if the source is "not-shielded" or the shield is in a "non-shielding position". In some examples of the present invention, shielded sources 34 have magnetic field strengths outside of such shielding of less than 10 Gauss (1 mT). In some examples of the present invention, shielded sources 34 have magnetic field strengths outside of such shielding of less than 5 Gauss (0.5 mT). It is noted that in the sectional illustrations of the examples described herein, regions intended to function as shields for source 34 are generally shown with the most dense hatching and may or may not be particularly numbered.

Referring to FIGS. 5A and 5B, schematic sectional views of a first example embodiment of first component 32 (similar to the view of FIG. 4) is shown in which source 34 is in an unshielded (FIG. 5A) and a shielded (FIG. 5B) positioning. In such embodiment, source 34 is movable (e.g., via a thumb or forefinger) via a manually actuated external slider arrangement 44 (e.g., similar to a utility knife) in and out of a stationary/fixed shielded region 42. Accordingly, when coupling such embodiment of first component 32 with second component 36, the patient/user must position source 34 in the unshielded position, and conversely when uncoupling such embodiment the patient/user must position source 34 in the shielded position. FIGS. 6A and 6B show an example that uses a manually activated slider arrangement 46 similar to external slider arrangement 44 of FIGS. 5A and 5B except slider arrangement 46 moves shield member 40 between a non-shielding (FIG. 6A) and a shielding (FIG. 6B) positioning while source 34 is stationary.

In contrast to the example "manual" or "active" embodiments of first component 32 shown in FIGS. 5A and 5B, as well as FIGS. 6A and 6B which require the patient/user to effectively activate or deactivate the magnetic fields emanating from source 34, the example embodiments of FIGS. 7A and 7B, as well as FIGS. 8A and 8B illustrate some "automatic" or "passive" arrangements of first component

32 where such activation/deactivation is accomplished during normal operation. Such functionality is provided by forming first component 32 from a main body portion 32A (that includes a shielded region 42) and an end portion 32B (that includes source 34) that is slidably coupled to main body portion 32A so as to be slidable outward from main body portion 32A. A biasing element 48 (e.g., a spring or other suitable structure) is provided between main body portion 32A and end portion 32B that biases end portion 32B into the fully inward positioning relative to main body portion 32A shown in FIG. 7B when no force is applied pulling end portion 32B outward from main body portion 32A.

However, when a sufficient force (e.g., tensioning force T of FIG. 7A) is applied pulling end portion 32B outward from main body portion 32A (and thus outward from rear headgear portion 20 as shown in FIG. 1), such as when a patient/user would grasp end portion 32B near an outward end 50 to bring first component 32 forward to engage with second component 36 (e.g., patient interface 10), end portion 32B moves outward from main body portion 32A and thus source 34 moves out from shielded region 42, thus "automatically" or "passively" moving from the shielded positioning of FIG. 7B to the unshielded positioning of FIG. 7A. Conversely, when first component 32 is uncoupled from second component 36, and thus the tensioning force T is removed, end portion 32B is biased back into main body portion 32A by biasing member 48, thus "automatically" or "passively" returning from the unshielded positioning of FIG. 7A to the shielded positioning of FIG. 7B. The example embodiment of first component 32 shown in FIGS. 8A and 8B functions in a similar manner as that shown in FIGS. 7A and 7B except such arrangement uses an outer biasing element 51 that can be forcibly stretched (e.g., by force tensioning force T) to the unshielded positioning shown in FIG. 8A, and will return to the generally relaxed (shielded) positioning shown in FIG. 8B. Outer biasing element 51 may be a nylon/spandex outer covering, or any other suitable arrangement.

Figures 9A, 9B:
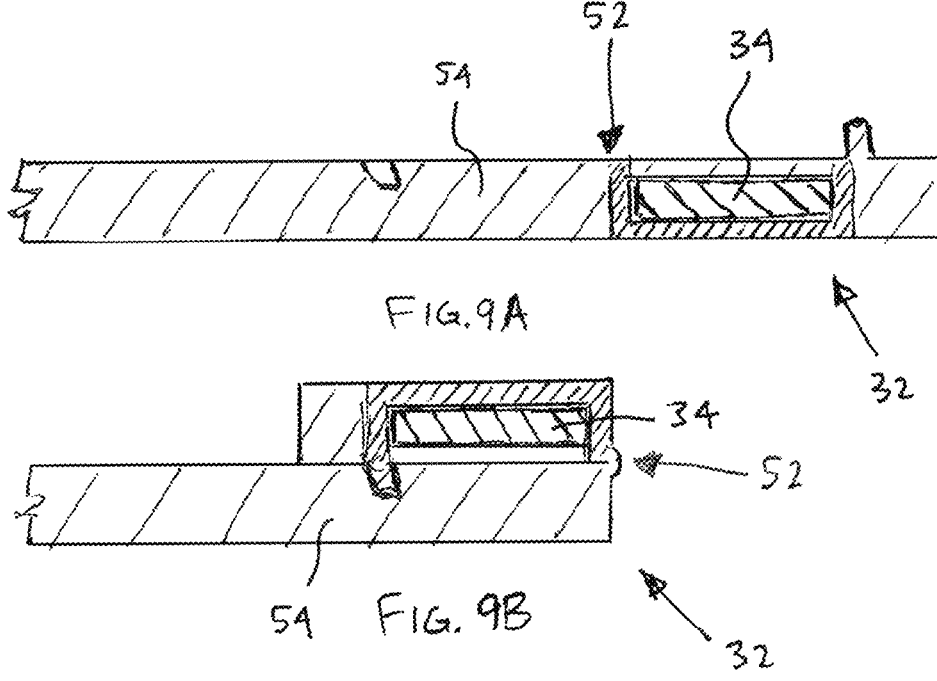
FIG. 9A is a schematic sectional view of a first component of a coupling arrangement in accordance with one example embodiment of the present invention shown with a source of a magnetic field in an unshielded positioning.
FIG. 9B is a schematic sectional view of the first component of FIG. 9A shown with the source of the magnetic field positioned in a shielded positioning.

Referring lastly to FIGS. 9A and 9B, an example embodiment of first component 32 is shown that utilizes a hinge portion 52 that provides for source 34 to be movable among an unshielded positioning (FIG. 9A) and a shielded positioning (FIG. 9B). Hinge portion 52 may be formed as a unitary portion of a main body 54 of first component or as a separate hinge arrangement coupling portions (not numbered) of first component 32 together. Hinge portion 52 may be structured so as to be biased in the shielded positioning shown in FIG. 9B, thus only moving to the unshielded positioning shown in FIG. 9A when actively being coupled to second component 36 by a patient/user. As an alternative to such arrangement, only a shield (e.g., similar to shield 40 of FIGS. 6A and 6B) could be moved via a hinge portion to selectively shield or unshield source 34.

From the foregoing it is thus to be appreciated that embodiments of the present invention provide coupling arrangements that utilize sources of magnetic fields in manners that such fields can be safely shielded, either actively or passively, so as to not interfere with sensitive medical devices.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A coupling arrangement for use in securing a patient interface to the head of a patient, the coupling arrangement comprising:
   a first component comprising a source of a magnetic field;
   a second component comprising a mating component attracted to the source of the magnetic field; and
   a shield component, wherein one or both of the source of the magnetic field and the mating component is moveable relative to the shield component among:
      a shielded positioning wherein the source of the magnetic field is shielded from the mating component by the shield component such that a maximum strength of the magnetic field outside of the first component is less than a predetermined value, and
      an unshielded positioning wherein the source of the magnetic field is unshielded from the mating component by the shield component such that the maximum strength of the magnetic field outside of the first component is greater than or equal to the predetermined value.

2. The coupling arrangement of claim 1, wherein the source of the magnetic field is moveable relative to the shield component.

3. The coupling arrangement of claim 1, wherein the source of the magnetic field comprises a permanent magnet.

4. The coupling arrangement of claim 1, wherein the portion of the mating component is moveable relative to the shield component.

5. The coupling arrangement of claim 1, wherein the second portion further comprises a patient interface.

6. The coupling arrangement of claim 5, wherein the first portion further comprises a frame member of a headgear arrangement.

7. The coupling arrangement of claim 1, wherein one or both of the source of the magnetic field and the mating component is moveable relative to the shield component in a sliding motion among the shielded and unshielded positionings.

8. The coupling arrangement of claim 1, wherein:
   the first component comprises:
      a main body portion having a shielded region defined therein defining the shield component, and
      an end portion slidably coupled to the main body portion, the end portion having the source of the magnetic field coupled therein; and
   the end portion and the source of the magnetic field are moveable among the shielded positioning and the unshielded positioning.

9. The coupling arrangement of claim 8, wherein the first component further comprises a biasing element biasing the end portion and the source of the magnetic field in the shielded positioning.

10. The coupling arrangement of claim 9, wherein the biasing element is provided as an internal element of the first component.

11. The coupling arrangement of claim 9, wherein the biasing element is provided as an external element of the first component.

12. The coupling arrangement of claim 1, wherein the first component further comprises a hinge portion structured to move the source of the magnetic field relative to the shield component.

13. The coupling arrangement of claim 12, wherein the hinge portion is structured to bias the source of the magnetic field in the shielded positioning.

14. A mask for communicating a flow of breathing gas to an airway of a patient, the mask having a coupling arrangement comprising:
   a first component comprising a source of a magnetic field;
   a second component comprising a mating component attracted to the source of the magnetic field; and
   a shield component, wherein one or both of the source of the magnetic field and the mating component is moveable relative to the shield component among:
   a shielded positioning wherein the source of the magnetic field is shielded from the mating component by the shield component such that a maximum strength of the magnetic field outside of the first component is less than a predetermined value, and
   an unshielded positioning wherein the source of the magnetic field is unshielded from the mating component by the shield component such that the maximum strength of the magnetic field outside of the first component is greater than the predetermined value.

* * * * *